United States Patent
Chen

(10) Patent No.: US 9,675,548 B2
(45) Date of Patent: Jun. 13, 2017

(54) ORALLY DISSOLVING FILMS

(75) Inventor: Li-Lan Chen, Parsippany, NJ (US)

(73) Assignee: GlaxoSmithKline, LLC, Wilmington, DE (US)

( * ) Notice: Subject to any disclaimer, the term of this patent is extended or adjusted under 35 U.S.C. 154(b) by 1414 days.

(21) Appl. No.: 10/565,706

(22) PCT Filed: Jul. 22, 2004

(86) PCT No.: PCT/US2004/023719
§ 371 (c)(1),
(2), (4) Date: Jan. 23, 2006

(87) PCT Pub. No.: WO2005/009386
PCT Pub. Date: Feb. 3, 2005

(65) Prior Publication Data
US 2006/0198873 A1  Sep. 7, 2006

Related U.S. Application Data

(60) Provisional application No. 60/489,855, filed on Jul. 24, 2003.

(51) Int. Cl.
| A61K 9/00 | (2006.01) |
|---|---|
| A61K 9/70 | (2006.01) |
| A61K 47/32 | (2006.01) |
| A61K 31/4439 | (2006.01) |
| A61K 31/465 | (2006.01) |
| A61K 31/724 | (2006.01) |

(52) U.S. Cl.
CPC ............ *A61K 9/0056* (2013.01); *A61K 9/006* (2013.01); *A61K 9/7007* (2013.01); *A61K 31/4439* (2013.01); *A61K 31/465* (2013.01); *A61K 31/724* (2013.01); *A61K 47/32* (2013.01)

(58) Field of Classification Search
None
See application file for complete search history.

(56) References Cited

U.S. PATENT DOCUMENTS

| 4,876,092 A | 10/1989 | Mizobuchi et al. |
| 4,933,182 A * | 6/1990 | Higashi et al. ................ 424/435 |
| 5,456,745 A * | 10/1995 | Roreger et al. ............. 106/140.1 |
| 5,508,276 A * | 4/1996 | Anderson et al. ............ 514/183 |
| 5,599,554 A | 2/1997 | Majeti |
| 5,603,947 A | 2/1997 | Wong et al. |
| 5,730,999 A | 3/1998 | Lehman et al. |
| 5,948,430 A | 9/1999 | Zerbe et al. |
| 6,063,399 A | 5/2000 | Assmus et al. |
| 6,077,541 A | 6/2000 | Chen et al. |
| 6,177,096 B1 | 1/2001 | Zerbe et al. |
| 6,183,775 B1 | 2/2001 | Ventouras |
| 6,197,331 B1 * | 3/2001 | Lerner et al. .................. 424/448 |
| 6,248,760 B1 | 6/2001 | Wilhemsen |
| 6,264,981 B1 | 7/2001 | Zhang et al. |
| 6,284,264 B1 | 9/2001 | Zerbe et al. |
| 6,420,473 B1 | 7/2002 | Chittamuru et al. |
| 6,420,573 B1 | 7/2002 | Campbell et al. |
| 6,479,076 B2 | 11/2002 | Blank |
| 6,552,024 B1 | 4/2003 | Chen et al. |
| 6,592,887 B2 | 7/2003 | Zerbe et al. |
| 6,709,671 B2 | 3/2004 | Zerbe et al. |
| 2001/0022964 A1 | 9/2001 | Leung et al. |
| 2001/0046511 A1 | 11/2001 | Zerbe et al. |
| 2002/0001880 A1 | 1/2002 | Kobayashi |
| 2002/0018800 A1 | 2/2002 | Pinney et al. |
| 2002/0054913 A1 | 5/2002 | Heese et al. |
| 2002/0058068 A1 | 5/2002 | Houze et al. |
| 2002/0150544 A1 | 10/2002 | Zerbe et al. |
| 2003/0049307 A1 | 3/2003 | Gyurik |
| 2003/0054038 A1 * | 3/2003 | Crew ................... A61K 9/143 424/486 |
| 2003/0068376 A1 * | 4/2003 | Chen et al. ................... 424/484 |
| 2003/0068378 A1 | 4/2003 | Chen et al. |
| 2003/0092724 A1 | 5/2003 | Kao et al. |
| 2003/0099691 A1 | 5/2003 | Lydzinski et al. |
| 2003/0099692 A1 | 5/2003 | Lydzinski et al. |
| 2003/0107149 A1 | 6/2003 | Yang et al. |
| 2003/0118653 A1 | 6/2003 | Chen et al. |
| 2003/0170195 A1 | 9/2003 | Houze et al. |
| 2003/0170295 A1 | 9/2003 | Kim et al. |
| 2003/0176467 A1 | 9/2003 | Andersson et al. |
| 2004/0013752 A1 | 1/2004 | Wolfson |
| 2004/0028732 A1 | 2/2004 | Falkenhausen et al. |
| 2004/0037879 A1 * | 2/2004 | Adusumilli et al. .......... 424/468 |
| 2004/0054551 A1 | 3/2004 | Ausubel et al. |
| 2004/0096490 A1 | 5/2004 | Bracht et al. |
| 2004/0096501 A1 | 5/2004 | Vaya et al. |
| 2004/0126330 A1 | 7/2004 | Awamura et al. |
| 2004/0191322 A1 | 9/2004 | Hansson |
| 2004/0241219 A1 | 12/2004 | Hille et al. |
| 2005/0181050 A1 | 8/2005 | Hirsh et al. |
| 2005/0226823 A1 | 10/2005 | Krumme et al. |
| 2005/0255048 A1 | 11/2005 | Hirsh et al. |
| 2005/0276842 A1 | 12/2005 | Zhang et al. |
| 2006/0018933 A1 | 1/2006 | Vaya et al. |
| 2006/0018934 A1 | 1/2006 | Vaya et al. |
| 2006/0045868 A1 | 3/2006 | Meezan et al. |
| 2006/0045869 A1 | 3/2006 | Meezan et al. |

(Continued)

FOREIGN PATENT DOCUMENTS

| CL | 200201344 | 6/2002 |
| EP | 0490944 | 3/1991 |

(Continued)

OTHER PUBLICATIONS

Lamosa et al. ("Design of Microencapsulated Chitosan Microspheres for Colonic Drug Delivery"), Journal of Controlled Release, 52 (1998) 109-118.*

(Continued)

*Primary Examiner* — Isis Ghali
(74) *Attorney, Agent, or Firm* — Joshua C. Sanders

(57) ABSTRACT

Rapidly dissolving, oral film preparations for rapid release of an active agent in the oral cavity, in particular, rapidly dissolving oral films comprising a nicotine active which achieve good transbuccal absorption and provide nicotine craving relief to an individual are disclosed herein.

9 Claims, No Drawings

(56) References Cited

U.S. PATENT DOCUMENTS

| | | |
|---|---|---|
| 2006/0046962 A1 | 3/2006 | Meezan et al. |
| 2006/0046969 A1 | 3/2006 | Maggio |
| 2006/0078604 A1 | 4/2006 | Kanios et al. |
| 2006/0084656 A1 | 4/2006 | Ziegler et al. |
| 2006/0233870 A1 | 10/2006 | Houze et al. |
| 2006/0240087 A1 | 10/2006 | Houze et al. |
| 2006/0286160 A1 | 12/2006 | Satoda et al. |
| 2007/0059346 A1 | 3/2007 | Maibach |
| 2007/0155774 A1 | 7/2007 | Moormann et al. |
| 2007/0190117 A1 | 8/2007 | Asmussen et al. |
| 2007/0202057 A1 | 8/2007 | Fankhauser et al. |
| 2007/0269386 A1 | 11/2007 | Steen et al. |
| 2007/0298090 A1 | 12/2007 | Chen et al. |
| 2008/0260807 A1 | 10/2008 | Sharp et al. |
| 2008/0286340 A1 | 11/2008 | Andersson et al. |
| 2008/0292683 A1 | 11/2008 | Sanghvi et al. |
| 2009/0081294 A1 | 3/2009 | Gin et al. |
| 2009/0253754 A1 | 10/2009 | Selmin et al. |
| 2010/0028447 A1 | 2/2010 | Letchworth et al. |
| 2010/0041703 A1 | 2/2010 | Sournac et al. |
| 2010/0063110 A1 | 3/2010 | Meyer et al. |
| 2010/0240724 A1 | 9/2010 | Chang et al. |
| 2010/0247586 A1 | 9/2010 | Hugerth et al. |
| 2010/0266669 A1 | 10/2010 | Meyer et al. |
| 2012/0156229 A1 | 6/2012 | Park et al. |
| 2013/0011462 A1 | 1/2013 | Bruce et al. |
| 2013/0039967 A1 | 2/2013 | Meyer et al. |

FOREIGN PATENT DOCUMENTS

| | | |
|---|---|---|
| EP | 0751873 | 11/1998 |
| EP | 1317916 | 6/2003 |
| EP | 1578422 | 4/2007 |
| JP | A 8-245423 | 9/1996 |
| WO | WO 96/22083 | 7/1996 |
| WO | WO 97/42941 | 11/1997 |
| WO | WO9802188 | 1/1998 |
| WO | WO 02076211 A1 * | 10/2002 |
| WO | WO 03/000292 | 1/2003 |
| WO | WO 03/026629 | 4/2003 |
| WO | WO03039518 | 5/2003 |
| WO | WO 2004/060298 | 7/2004 |
| WO | WO2004054551 | 7/2004 |
| WO | WO 2005/004989 | 1/2005 |
| WO | WO2005048980 | 6/2005 |
| WO | WO 2006/114604 | 11/2006 |
| WO | WO2009045022 | 4/2009 |
| WO | WO2009074552 | 6/2009 |
| WO | WO2010/044736 | 4/2010 |
| WO | WO2012/039775 | 3/2012 |

OTHER PUBLICATIONS

Polymethacrylate, "Handbook of Pharmaceutical Excipients", Arther H. Kibbe, 3rd ed., pp. 401-406 (2000).*
CL200201344 (abstract translation only).
http://eudragit.evonik.com/product/eudragit/en/products-services/eudragit-products/enteric-formulations/l-100/pages/default.aspx ; accessed Feb. 6, 2013.
http://eudragit.evonik.com/product/eudragit/en/products-services/eudragit-products/enteric-formulations/s-100/Pages/default.aspx ; accessed Feb. 6, 2013.

* cited by examiner

ORALLY DISSOLVING FILMS

This application is a 371 of International Application No. PCT/US2004/023719, filed 22 Jul. 2004, which claims the benefit of U.S. Provisional Application No. 60/489,855, filed Jul. 24, 2003.

FIELD OF THE INVENTION

The present invention relates to rapidly dissolving, oral film preparations for release of an active agent in the oral cavity. In one embodiment the invention relates to rapidly dissolving oral films comprising a nicotine active which achieve good transbuccal absorption and provide nicotine craving relief.

BACKGROUND OF THE INVENTION

It is generally known that the smoking of tobacco products, such as cigarettes, cigars, and pipe tobacco, presents serious health risks to the user and those subjected to second hand smoke. It is also known that the use of other forms of tobacco, such as chewing tobacco, can also result in serious health risks to the user.

Although the damaging effects of tobacco smoking are well known, most individuals with nicotine dependence have great difficulty in overcoming the dependence. The difficulty arises, in large part, due to the addictive nature of nicotine. Overcoming nicotine craving is the critical challenge for those attempting to conquer nicotine dependence. These cravings may arise in several ways. For instance, studies have shown that following a quit attempt, smokers report moderate levels of steady nicotine craving throughout the day. Those who more intensely crave nicotine are more likely to relapse and return to using tobacco. In addition to steady cravings, smokers also experience episodic, or acute, cravings. These acute cravings can be provoked by a variety of stimula, such as exposure to smoking related cues, seeing smoking paraphernalia or others smoking, or inhaling second hand smoke. Such episodic craving can also result in relapse if proper coping measures are not employed.

In recent years, Nicotine Replacement Therapies (NRTs) have been successfully commercialized as a means to reduce or quit smoking, chewing and other methods of tobacco usage. NRT is generally effective to temporarily replace some of the nicotine that is lost when a user quits using tobacco. Such commercial NRTs include nicotine gums (e.g. NICORETTE®) and transdermal nicotine patch systems (e.g. NICODERM®, NICOTROL®, PROSTEP® and HABITROL®). Generally, transdermal nicotine patches are useful for maintaining relatively steady blood level concentrations over time by providing the user with a substantially continuous infusion of nicotine while the patch is worn. Likewise, when used at regular intervals, nicotine gum can maintain relatively steady blood nicotine concentrations over time. Thus, both the nicotine patch and the nicotine gum can be effective against the steady nicotine craving experienced by an individual in the process of quitting tobacco usage. However, those individuals more prone to intense and acute nicotine cravings may desire more rapid, or intermittent, craving relief than typically provided by a transdermal nicotine patch.

In some circumstances, nicotine gum can be used to relieve the acute cravings experienced by the individual that is attempting to quit smoking or other tobacco use. For example, a single piece of gum may be self-administered by an individual in response to an acute nicotine craving. Such use of the nicotine gum typically results in an increase in blood nicotine levels to counteract the nicotine craving, however, the gum tends to release nicotine somewhat slowly in the oral cavity and may not provide relief as quickly as the individual would like. In addition, this intermittent gum use would not be as effective against the more constant nicotine cravings.

Nicotine lozenges are also commercially available and may be utilized in a similar manner to provide relief from acute nicotine cravings. Currently available nicotine lozenges include, for example, COMMIT®, STOPPERS®, NIQUITIN®, and NICOTINELL® brand lozenges. Like the nicotine gum, a user may self-administer the lozenge in response to a nicotine craving and the lozenge will slowly release nicotine in the oral cavity.

However, a limitation of both the gum and lozenge NRT product forms is that they each have an average oral retention time of about 20 minutes to obtain the maximum benefit. Thus, craving relief may not be as fast as the individual would like. Further, due to this required oral retention time, users may administer the gum or lozenges less frequently than is actually needed or recommended, possibly resulting in more frequent nicotine cravings. For example, an individual may continue to chew the nicotine gum long after the majority of the available nicotine active has been consumed and may not realize that the gum has been exhausted and nicotine cravings may then result.

Thus, while existing NRT means may have some utility in helping to cope with steady and acute tobacco cravings, there is still an ongoing need to provide faster and more effective craving relief, as well as to provide other more convenient product forms.

Nicotine has been incorporated into water soluble films which generally comprise highly hydrohilic polymers to dissolve in the oral cavity and release nicotine for buccal absorption. In order to achieve fast dissolution, the water-soluble polymers typtically employed in these films have high hydration rates and result in a very hygroscopic film. Due to the volatile nature of nicotine, however, films of this type generally result in compromised nicotine stability.

Several patents within the same patent family have issued to Zerbe et al. relating to mucoadhesive films. U.S. Pat. No. 5,948,430, reexamined at 90/005887, relates to a monolayer film formed from a mucoadhesive composition comprising: at least one water soluble polymer; a surfactant alone or in combination with at least one member selected from the group consisting of a polyalcohol and a plasticizer, or a polyalcohol and a plasticizer; at least one cosmetic or pharmaceutical ingredient and a flavoring agent; said film being one which rapidly softens and completely disintegrates in the oral environment and having dry film thickness which is suitable for application into the mouth without causing adverse feeling in the mouth. U.S. Pat. No. 6,709,671 relates to various monolayer films formed from a mucoadhesive composition comprising: at least one water soluble polymer; a surfactant, an active and additional components, such as a water-dispersible polymer. U.S. Pat. No. 6,177,096 relates to a composition comprising at least one water soluble polymer, at least one polyalcohol, and at least one active agent, wherein the composition has mucoadhesive properties. U.S. Pat. No. 6,284,264 relates to methods for releasing an active agent into the oral cavity by applying a mucoadhesive film comprising the active into the oral cavity of a person, allowing the mucoadhesive film to dissolve within the oral cavity and releasing the active into the oral cavity, more specifically releasing the active agent to the patient via the mucous membrane. U.S. Pat. No.

6,592,887 relates to the same method for releasing an active agent into the oral cavity but specifically requires that the active agent be nicotine. The disclosures of each of these patents contain examples of a dry film wherein nicotine salicylate is the pharmaceutical ingredient used, and where the composition also comprises hydroxypropylmethyl cellulose, polyvinylpyrrolidone, a flavoring agent and a colorant.

European Pat. No. Application EP1 008 343 A1 to Kyukyu Pharmaceutical Co., relates to a film preparation mainly comprising a drug, an edible polymer and a saccharide, which is rapidly soluble in the oral cavity.

PCT Application, WO 00/42992 relates to a dosage unit comprising a water-soluble hydrocolloid, mucosal surface coat-forming film, where the film includes an effective dose of an active agent. The film can be hydroxypropylmethyl cellulose polymer and the active agent can be nicotine. The film, on contact with the moist mucosal surface of the mouth, becomes a coating that adheres to the mucosal surface and then disintegrates and dissolves to release the active agent.

PCT Application WO 02/43657 discloses pullulan free edible film compositions comprising effective amounts of at least one film forming agent, at least one bulk filler agent and at least one plasticizing agent.

PCT Application WO 01/70194 to Warner Lambert Company 7 broadly relates to consumable films adapted to adhere and dissolve in the mouth of a consumer, wherein the film comprises at least one water soluble polymer, at least one active agent and at least one taste masking agent.

As far as the inventors of the instant invention are aware, the nicotine containing orally dissolving films described above, do not address the difficulty associated with effectively driving transbuccal absorption of nicotine and maintaining nicotine stability. Therefore, there remains a need for a rapidly dissolving oral film that effectively delivers a nicotine active to a user in a sufficient amount to reduce or eliminate the steady or acute nicotine cravings associated with quitting tobacco usage.

SUMMARY OF THE INVENTION

The present invention relates to rapidly dissolving oral film compositions for release of an active agent in the oral cavity. In one embodiment the rapidly dissolving oral films comprise an enteric polymer, an alkaline neutralizing agent, and an active agent, such as nicotine base. It is believed that the active agent will form a water-insoluble complex with the enteric polymer and that the resulting hydrophobic film will not take up water, thus improving shelf life and stability of the active. Upon application to the oral cavity the alkaline neutralizing agent will dissolve to increase the pH level in the mouth. As the pH is increased the enteric polymer will dissolve and release nicotine in the oral cavity for tranbuccal absorption. The increase in the pH of the oral cavity will also serve to enhance transbuccal absorption of nicotine. Alternatively, an additional alkaline buffering agent may be provided within the film composition of the present invention to enhance the transbuccal absorption of nicotine.

In another embodiment the enteric polymer used in the film compositions is pre-neutralized during preparation of the film compositions. Where pre-neutralized enteric polymers are utilized, the final formulation contains at least one additional alkaline buffering agent to help drive nicotine absorption. The alkaline neutralizing agent and/or the additional alkaline buffering agents employed in the present invention may be present in two separate components within the film formulation in order to avoid the nicotine active from adversely reactive with the alkaline buffering agent prior to administration.

The films compositions of the present invention may further comprise plasticizers, additional active agents, flavorants, sweeteners, taste-masking agents, sensory impact agents, water-soluble fillers, surface and release modifiers, colorants, chelating agents, polyglycols, thickeners, and the like.

In one embodiment, the film comprises a first component comprising a nicotine active, a neutralized enteric polymer and a plasticizer and a second component comprising a buffering agent and a water-soluble filler.

The present invention also relates to orally dissolving film compositions which delivers both rapid and sustained release of an active agent. In one embodiment, wherein the composition comprises a first component comprising an enteric polymer or a film-forming polymer, an active agent such as a nicotine active, and at least one alkaline neutralizing agent which may be seperately maintained; and a second component comprising an active agent and a bioadhesive polymer wherein the second component provides sustained release of nicotine to an individual. In one embodiment the bioadhesive polymer is a polymer capable of forming a hydrogen bond with nicotine.

These orally dissolving film compositions are useful as a stand alone nicotine replacement therapy (NRT) or for improving compliance with an alternate Nicotine Replacement Therapy. Such orally dissolving film compositions provide can be used to provide rapid, sustained or combination nicotine craving relief to an individual in need thereof.

DETAILED DESCRIPTION OF THE INVENTION

All publications including, but not limited to, patents and patent applications cited in this specification are incorporated herein by reference as though fully set forth.

Unless otherwise specified all parts and percentages set forth herein are weight percentages based on the total weight of the relevant orally dissolving film being described.

Unless otherwise stated as used herein, the term "a" or "an" includes one or more of the components modified.

The present invention may comprise, consist of, or consist essentially of the components set forth below, unless otherwise stated.

The present invention relates to rapidly dissolving, oral film preparations for release of an active agent. In one embodiment the invention relates to rapidly dissolving oral films comprising a nicotine active which achieve good transbuccal absorption and provide nicotine craving relief to an individual in need thereof.

As used herein, the term "nicotine active" refers to one or more compounds selected from: nicotine; derivatives of nicotine, such as nicotine salts and nicotine complexes; tobacco extract or leaf; any compounds or compositions that produce a similar physiological effect as nicotine, such as lobeline; and mixtures thereof. A variety of nicotine actives are well known in the art and are commercially available. Suitable nicotine actives for use herein include, but are not limited to, nicotine monotartrate, nicotine bitartrate, nicotine hydrochloride, nicotine dihydrochloride, nicotine sulfate, nicotine zinc chloride monohydrate, nicotine salicylate, nicotine oil, nicotine complexed with cyclodextrin, polymer resins such as nicotine polacrilex, and mixtures thereof. The nicotine active may be used in one or more distinct physical forms well known in the art, including free base forms, encapsulated forms, ionized forms and spray-dried forms.

The orally dissolving films of the present invention comprise one or more nicotine actives in an amount sufficient to reduce nicotine cravings. In certain embodiments, the amount of nicotine active is effective to reduce nicotine cravings either rapidly (e.g. within about 10 minutes, in one embodiment within about 5 minutes), over a sustained period (e.g. for up to 5 hours, alternatively up to 2 hours, or alternatively up to about 1 hour), or both. In one embodiment the nicotine active present in the formulation is nicotine at a level of from about 0.1 mg to about 5 mg. In another embodiment the nicotine active in the formulation is lobeline at a level of 0.1 mg to about 5 mg.

The term "enteric polymers" as used herein is meant to describe those ionisable polymers that have pH sensitive solubility, such as phthalate esters and acrylics. Generally, these polymers have ionisable carboxyl groups that pass unionized in the acid stomach, but become ionized in the higher pH environment of the intestine and hence become soluble. In the present invention, the alkaline buffering agents present in the film compositions, once administered to the oral cavity of an individual and in contact with saliva, cause the pH to rise in the oral cavity. As a result, these enteric polymers are thus ionozed in the oral cavity and the film composition quickly disintegrates. In one embodiment of the present invention, the active agent is nicotine base which forms a water-insoluble complex with the enteric polymer. Upon administration in the oral cavity, the alkaline buffer alters the pH of the oral cavity, thereby dissolving the enteric polymer and rapidy releasing the nicotine in the oral cavity for transbuccal absorption. In another embodiment of the present invention, the enteric polymer is pre-neutralized during processing of the film composition. Thus, upon application to the oral cavity the film will dissolve in saliva. Suitable enteric polymers for use in the present invention include but are not limited to cellulose acetate phthalate, hydroxypropyl methylcellulose phthalate, polyvinylacetate phthalate, poly(ethylacrylate methacrylic acid) copolymer, shellac, hydroxypropyl methylcellulose acetate succinate, poly(methyl vinyl ether/maleic acid) monoethyl ester, and poly(methyl vinyl ether/maleic acid) n-butyl ester.

An alkaline neutralizing agent, or buffering agent, is incorporated in the films of the instant invention. The buffering agent or agents serve dual purposes in the films of the present invention. The buffering agent should be present in sufficient quantity to neutralize the enteric polymer present in the film composition and also to enhance transbuccal absorption of the nicotine active by raising the pH of the mouth saliva to alkaline levels. In one embodiment the neutralization of the enteric polymer occurs in the oral cavity. The film composition comprises an enteric polymer, an alkaline neutralizing agent, a nicotine active and, optionally, an additional alkaline buffering component. The alkaline neutralizing agent may or may not be the same as the alkaline buffering agent. Where present, the alkaline neutralizing agent, the alkaline buffering agent, the nicotine active, or any combination thereof, may be separately maintained prior to administration.

In one embodiment, the enteric polymer is pre-neutralized prior to forming the film compositions. Where the enteric polymer is pre-neutralized, an additional alkaline buffering agent is incorporated into the film to enhance transbuccal absorption of nicotine. The buffering agent(s) should be separately maintained from the nicotine active prior to administration. To drive nicotine absorption, suitable buffer materials for use include organic and inorganic bases which have the capability to provide a mouth saliva pH from above 7 to about 12, in one embodiment from above 7 to about 11, in another embodiment from above 7.5 to about 10, and in yet another embodiment from above 7.5 to about 9.

Examples of suitable buffers for use in the present invention include, but are not limited to, sodium carbonate, sodium bicarbonate, potassium carbonate, potassium bicarbonate, sodium phosphate dibasic, sodium phosphate tribasic, potassium phosphate dibasic, potassium phosphate tribasic, calcium carbonate, magnesium carbonate, sodium hydroxide, magnesium hydroxide, potassium hydroxide, aluminium hydroxide, and combinations thereof.

Where at least one or a portion of one of the neutralizing or buffering agent(s) is separately maintained from the nicotine active, this may be achieved by any means known in the art, such as independent encapsulation of one or both components prior to formulation, separating the components in distinct layers as in a laminate structure, or in jet printing of one component onto a film containing the other component, etc.

In another embodiment, the present invention provides both rapid and sustained release of an active agent. Where the active agent is a nicotine active, the film composition provides both rapid and sustained nicotine craving relief by providing a rapid nicotine release component and a sustained nicotine release component. The rapidly releasing nicotine active component comprises: an enteric polymer or a film-forming polymer or a mixture thereof; a first nicotine active; and at least one buffering agent. The buffering agent and the nicotine active may be separated by any means known in the art to avoid interaction prior to administration. The sustained release component comprises a second nicotine active and a bioadhesive material that is capable of forming a hydrogen bond with said second nicotine active. The rapidly releasing component and the sustained release components may be separately prepared and then combined by any means known in the art and processed into an orally dissolving film form. Alternatively, the components may be maintained separately until administered to the individual, such as in separate layers of a multilayer film, or through encapsulation of one or both components.

Upon administration of the film, the rapid release component dissolves in the oral cavity releasing nicotine. Within the sustained release component, it is believed that the nicotine active and the bioadhesive material, form a bioadhesive-nicotine complex that subsequently adheres to the oral mucosa. The bioadhesive-nicotine complex remains adhered to the mucosal tissues of the mouth and gradually releases nicotine in the oral cavity, providing for buccal absorption of nicotine over time. The bioadhesive-nicotine complex may remain adhered to the oral mucosa for up to 5 hours, in one embodiment for up to 2 hours, in another embodiment for up to about 1 hour.

Suitable bioadhesive materials for use in the present invention include any bioadhesive material capable of forming a hydrogen bond with a nicotine active. For example, bioadhesive polymers that contain hydrogen bonding functional groups such as alcohols, aldehydes, ketones and amides, may form hydrogen bonds with a nicotine active. Suitable bioadhesive materials include, but are not limited to, polyethylene oxide, chitosan, carbomers such as Carbopol 934, the non-ionic block polymer Pluronic F127, dextrans, polycarbophil, sodium alginate, and copolymers of maleic acid (MA) and an alkyl vinyl ether (AVE), such as the Gantrez-type polymers sold by ISP Corporation, in particular, Gantrez S-97. In one embodiment the bioadhesive polymer is polycarbophil. In another embodiment the bioadhesive polymer is a Gantrez-type polymer. Bioadhesive polymers may be present from about 1% to about 85% of the total weight of the film. In one embodiment, the bioadhesive polymer is present from about 5% to about 10% of the total weight of the film.

Where a rapid and sustained release film is contemplated, the rapid release component may comprise: a polymeric component selected from the group consisting of an enteric polymer in combination with a neutralizing agent, a pre-neutralized enteric polymer, a film-forming polymer or a mixture thereof; an alkaline buffering agent and an active agent such as a nicotine active. Film-forming polymers suitable for use in the present invention include, but are not limited to, a polyvinyl alcohol-polyethylene glycol graft copolymer of the general formula (I)

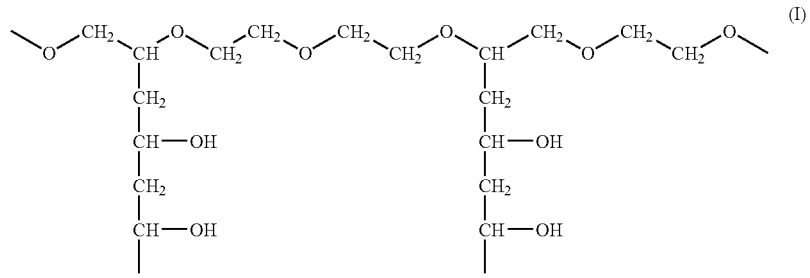

pullunan, hydroxypropylmethyl cellulose (HPMC), hydroxyethyl cellulose (HPC), polyvinyl pyrrolidone (PVP), carboxymethyl cellulose (CMC), polyvinyl alcohol (PVA), sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elisan, collagen, gelatin, zein, gluten, soy protein isolate, whey protein isolate, casein, and mixtures thereof. In one embodiment, the film-forming polymer is a polyvinyl alcohol-polyethylene glycol graft copolymer of the general formula (I). Generally, the polymeric materials are present in the rapid release component in amounts ranging from about 0.1% to about 99%, in one embodiment from about 30% to about 80%, in another embodiment from about 45% to about 70%.

It has been shown that the satisfaction derived from smoking and other forms of tobacco usage depends not only from the pharmacological effects of nicotine but also from the sensory stimulation that accompanies such usage. For example, the "tracheal scratch" is a particularly noticeable and frequent sensory stimulation that occurs when smoking tobacco. Sensory impact agents which provide similar sensory stimuli to that experienced with tobacco usage, or which provide alternative "distracting" stimuli, such as a strong burst of flavor, to the individual, may be useful to provide nicotine craving relief. Thus, the orally dissolving films of the present invention may comprise at least one sensory impact agent which may be any rapidly releasing, non-pharmacological component for providing a sensory signal effective to provide nicotine craving relief. The sensory signals affected may include taste, tactile or scent. Suitable sensory impact agents include, but are not limited to; impact flavors, such as capsiacin, mustard, horseradish, ginger, wasabi, smoke, and black pepper; mild irritants, such as denicotinized smoke, citric acid, ascorbic acid; and mixtures thereof. Such sensory impact agents may be added to the films of the present invention in an amount suitable to provide rapid craving relief to an individual. If present in sufficient quantity the sensory impact agent may provide a sufficient "distraction" to the individual that an additional rapid nicotine release component need not be provided to achieve nicotine craving relief.

The film compositions of the present invention may optionally include at least one plasticizer. Suitable plasticizers include, but are not limited to, benzyl benzoate, chlorobutanol, dibutyl sebacate, diethyl phthalate, glycerol, polyethylene glycol, sorbitol, triacetin and triethyl citrate. In one embodiment the plasticizer is triethyl citrate.

The orally dissolving films of the present invention may contain one or more additional optional ingredients including: taste modifiers, such as flavorants, sweeteners, and taste-masking agents; colorants; polyglycols, such as polyethylene glycol, propylene glycol and glycerol; chelating agents to prevent oxidation such as ethylenediaminetetraacetic acid (EDTA); fillers such as sorbitol, mannitol, sucrolose, lactose, sucrose, xylitol, silica, dextrates, glucose, fructose, sugars and trehalose, and emulsifiers such as surface and release modifiers including, but not limited to, castor oils, cetyl alcohol, and hydrogenated vegetable oils.

High intensity sweeteners are suitable for use herein and include, but are not limited to soluble saccharin salts (eg. sodium and calcium salts); the free acid form of saccharin; cyclamate salts; aspartame; and the potassium, calcium, sodium, and ammonium salts of 3,4-dihydro-6-methyl-1,2,3-oxathiazine-4-one-2,2-dioxide.

Suitable colorants include any pigments, dyes, lakes or natural food colors that are suitable for food and drug applications, eg. FD&C dyes and lakes.

Optionally other cosmetic or pharmaceutically active agents may be included in the films of the present invention. Examples of other suitable active agents include, but are not limited to, tooth whitening materials, breath fresheners, anti-cavity compounds, anti-calculus compounds, antioxidants, antiinflammatory agents, analgesics, antihistamines, local anesthetics, antibacterial compounds, disinfectants, vasoconstrictors, hemostatics, chemotherapeutics, antibiotics, tooth desensitizing agents, antifungals, vasodilators, antihypertensives, antiemetics, antimigraine, antiarrhythmics, antiasthmatics, antidepressants, vaccines, peptides or prodrugs, hormones, proton pump inhibitors, H2 receptor antagonists. In addition, vitamins and other dietary and nutritional supplements, such as vitamins C and E, are suitable for use in the film compositions described herein.

The orally dissolving films of the present invention are useful as a tobacco replacement. The film compositions are useful as a means to reduce or stop tobacco usage, including smoking tobacco (cigarettes, cigars, pipe tobacco) and chewing tobacco. The films may be used as a total or partial replacement of tobacco, and can be used concurrently with tobacco in any planned tobacco reduction program. Thus, the present invention also relates to methods of reducing tobacco usage, comprising orally administering one or more of the orally dissolving films of the present invention to a person in need of such reduction. The present invention also relates to methods of providing rapid and/or sustained relief from nicotine cravings by administering to an individual in need thereof, one or more of the orally dissolving films of the present invention.

In general, the films are administered as needed to prevent or reduce nicotine cravings, within any recommended or permitted limits. The orally dissolving films are typically administered such that the nicotine active is primarily delivered transbuccally in the mouth. Useful regimens may include those which provide a sustained nicotine blood plasma level of from about 6 ng/ml to about 35 ng/ml. Fast craving relief may be perceived by the user where, for example, the composition is configured to provide a plasma concentration of at least about 6 ng/ml, especially at least about 12 ng/ml, within about 10 minutes of starting administrations, especially within about 5 minutes of administration.

In one embodiment, in order to achieve craving relief the individual will consume one dosage unit of the orally dissolving film as needed to provide relief from or to prevent a nicotine craving. The films of the present invention are effective as a stand alone NRT regimen when taken frequently, from about 2 to about 4 times per hour.

EXAMPLES

Without further elaboration, it is believed that one skilled in the art can, using the preceding description, utilize the present invention to its fullest extent. The following examples, therefore, are to be construed as merely illustrative and not a limitation of the scope of the present invention.

Example 1

Illustrative examples of the dissolving film formulations of the present invention follow:
A single layer film is produced by the following process:
Solution Preparation—
(a) Weigh all excipients except EUDRAGIT® L100 55 (poly(methacylic-acid-co-ethyl acrylate) 1:1) and nicotine oil into a hydroalcohol/water solution (ethanol/water 60/40).
(b) Using high speed mixer, dissolve all solids in the hydroalchol/water solution.
(c) Increase the mixing speed and gradually add EUDRAGIT® L100 55 (poly(methacylic acid-co-ethyl acrylate) 1:1) powder into the hydroalcohol mixture.
(d) Continue mixing until neutralization process is complete and no more effervescence is detected.
(e) Reduce the mixing speed and add nicotine oil into EUDRAGIT® hydroalcohol solution.
(f) Cap the bottles and place it on the roller mixer for at least two hours for additional mixing and degassing
Casting Process—
(a) Cast the solution at about 10 to about 20 mil wet thickness on a polyethylene casting liner and dry it at about 60 degrees for about 10 minutes.
(b) A dry film thickness of from about 2 to about 4 mil thickness is obtained and may be die cut the film into about 2 mg nicotine unit doses.

Example 1

A Monolayer Nicotine Containing Film

| Ingredient | Dry % | Weight (mg) |
| --- | --- | --- |
| Nicotine Oil | 3.33 | 2.01 |
| EUDRAGIT ® L100 55 (poly(methacylic acid-co-ethyl acrylate) 1:1) | 52.25 | 31.38 |
| Triethyl Citrate | 26.62 | 15.96 |
| Intensates Cool Peppermint | 11.15 | 6.65 |
| Sucrolose | 2.16 | 1.33 |
| Sodium Bicarbonate | 4.49 | 2.66 |
| Disodium EDTA | 0.02 | 0.01 |
| Total | 100 | 60.0 |

Example 2

A Monolayer Nicotine Containing Film

| Ingredient | Dry % | Weight (mg) |
| --- | --- | --- |
| Nicotine Oil | 3.37 | 2 |
| EUDRAGIT ® L100 55 (poly(methacylic acid-co-ethyl acrylate) 1:1) | 50.08 | 29.7 |
| Triethyl Citrate | 25.30 | 15.0 |
| Intensates Cool Peppermint | 10.62 | 6.3 |
| Sucrolose | 2.02 | 1.2 |
| Sodium Bicarbonate | 8.60 | 5.1 |
| Total | 100 | 59.3 |

To produce a bilayer film, the enteric polymer (EUDRAGIT® L100 55 (poly(methacylic acid-co-ethyl acrylate) 1:1)), plasticizer (triethyl citrate), sweetener (Magasweet), taste masking agent (intensates), chelating agent (EDTA), neutralizing agent (sodium bicarbonate) and the active ingredient (nicotine oil) are dissolved in 60/40 (ethanol/water) hydroalcohol with the pH greater than 4 but less than 7 as described below.
Enteric Polymer Layer:
(a) Weigh all excipients except EUDRAGIT® L100 55 (poly(methacylic-acid-co-ethyl acrylate) 1:1) and nicotine oil into a hydroalcohol/water solution (ethanol/water 60/40).
(b) Using high speed mixer, dissolve all solids in the hydroalchol/water solution.
(c) Increase the mixing speed and gradually add EUDRAGIT® L100 55 (poly(methacylic acid-co-ethyl acrylate) 1:1) powder into the hydroalcohol mixture.
(d) Continue mixing until neutralization process is complete and no more effervescence is detected.
(e) Reduce the mixing speed and add nicotine oil into EUDRAGIT® hydroalcohol solution.
(f) Cap the bottles and place it on the roller mixer for at least two hours for additional mixing and degassing.
The second solution, i.e. the buffering solution, comprises the alkalizing agent but no film forming polymers. The buffering solution contains alkalizing agent (disodium phosphate), water soluble filler (lactose), sweetening agent (Megasweet), polyglycol (glycerin), flavoring agent (menthol), thickening agent (silica), and non-ionic emulsifying agent (polysorbate 80) in water. The buffering layer is prepared as follows:

Buffering Layer:
(a) Weigh all excipients except silica into water.
(a) Use high speed homogenizer to homogenize the mixture.
(b) Transfer the mixture into vacuum mixer container.
(c) Add silica into the mixture and vacuum mix silica into the dispersion.
(d) Transfer the dispersion to a capped bottle and place it on the roller mixer until use.

The polymer solution is subsequently casted on a polyethylene casting liner at a wet thickness of about 2 to about 4 mil, and is dried in an oven. A clear and glossy film is obtained after drying. The buffering layer is subsequently cast on top of the polymer layer and subsequently dried in an oven. The film should equilibrate at room condition for a day or two and then be may be die cut into about 2 mg nicotine unit doses.

Example 3A-3H

Depict Bilayer Films

| Ingredient | Ex. 3A wt (mg) | Ex. 3B wt (mg) | Ex. 3C wt (mg) | Ex. 3D wt (mg) |
|---|---|---|---|---|
| Layer 1 | | | | |
| Nicotine Oil | 2.0 | 2.0 | 2.0 | 2.0 |
| EUDRAGIT ® L100 55 (poly(methacylic acid-co-ethyl acrylate) 1:1) | 35.5 | 34.1 | 32.7 | 19.7 |
| EUDRAGIT ® NE 30 (Poly(ethyl acrylate-co-methacrylate) 2:1) | 0 | 0 | 0 | 8.6 |
| Polysorbate 80 | 0 | 0 | 0 | 11.1 |
| Triethyl Citrate | 10.9 | 17.1 | 22.7 | 0 |
| Intensates Cool Peppermint | 6.8 | 6.6 | 6.3 | 4.3 |
| Megasweet L100 | 4.1 | 3.9 | 3.8 | 2.6 |
| Sodium Bicarbonate | 0.7 | 1.3 | 2.5 | 1.7 |
| Layer 2 | | | | |
| Lactose | 86.9 | 83.3 | 79.7 | 94.2 |
| Sorbitol | 7.6 | 7.2 | 6.9 | 8.2 |
| Disodium Phosphate | 9.4 | 9.1 | 8.7 | 10.2 |
| Megasweet 100 | 3.8 | 3.6 | 3.5 | 4.1 |
| Silica | 2.8 | 2.7 | 2.6 | 3.1 |
| Intensates Cool Peppermint | 9.4 | 9.1 | 8.7 | 10.2 |
| Total Weight | 180.0 | 180.0 | 180.0 | 180.0 |

| Ingredient | Ex. 3E Dry % | Ex. 3F Dry % | Ex. 3G Dry % | Ex. 3H Dry % |
|---|---|---|---|---|
| Layer 1 | | | | |
| Nicotine Oil | 13.8 | 13.5 | 13.5 | 13.8 |
| EUDRAGIT ® L100 55 (poly(methacylic acid-co-ethyl- acrylate)1:1) | 42.2 | 40.4 | 40.4 | 42.2 |
| Sodium EDTA | 0.2 | 0.2 | 0.2 | 0.2 |
| Sodium Bicarbonate | 6.5 | 5.8 | 5.8 | 6.5 |
| Triethyl Citrate | 24.3 | 26.9 | 26.9 | 24.3 |
| Intensates Cool Peppermint | 8.1 | 9.0 | 9.0 | 8.1 |
| Megasweet L100 | 4.9 | 4.5 | 4.5 | 4.9 |
| Total | 100 | 100 | 100 | 100 |
| Layer 2 | | | | |
| Lactose | 68.6 | 68.6 | 52.8 | 52.8 |
| Polysorbate 80 | 0.7 | 0.7 | 0.7 | 0.7 |
| Disodium Phosphate | 7.1 | 7.1 | 7.3 | 7.3 |
| Megasweet 100 | 2.9 | 2.9 | 2.9 | 2.9 |
| Methanol | 7.1 | 7.1 | 7.3 | 7.3 |
| Silica | 2.2 | 2.2 | 2.6 | 2.6 |
| Sorbitol | 0 | 0 | 26.4 | 26.4 |
| Glycerin | 11.4 | 11.4 | 0 | 0 |
| Total | 100 | 100 | 100 | 100 |

Example 4 relates to a dissolving film comprising both rapid and sustained release components.

Example 4A

Rapid Release Component

| Ingredient | % w/w | Function | Amt/dose (mg) |
|---|---|---|---|
| Kollicoat ® IR | 75.19 | Polymer | 30.00 |
| KHCO3 | 1.10 | Buffer | 0.44 |
| Na2CO3 | 10.18 | Buffer | 4.06 |
| Glycerin | 7.52 | Plasticizer | 3.00 |
| Sucralose | 0.75 | Sweetener | 0.30 |
| Peppermint (oil) | 5.26 | Flavor | 2.10 |
| Water* | | | 120.00 mL |

*Not present in final formulation.

Example 4B

Sustained Release Component

| Ingredient | % | Function | Amt/Dose (mg) |
|---|---|---|---|
| Starch B990 | 2.00 | Polymer | 2.00 |
| Starch B760 | 15.00 | Polymer | 15.00 |
| Hydroxypropyl Cellulose | 5.00 | Polymer | 5.00 |
| Nicotine Bitartrate* | 20.00 | Active | 0.05 |
| Glycerin* | 15.00 | Plasticizer | 3.30 |
| PEG 8000* | 0.20 | Plasticizer | 0.04 |
| Silica* | 15.00 | Abrasive | 3.30 |
| Sodium Lauryl Sulfate* | 2.00 | Surfactant | 0.44 |
| Sucralose* | 0.50 | Sweetener | 0.11 |
| Peppermint (oil)* | 6.00 | Flavor | 1.32 |
| Menthol (oil)* | 2.00 | Flavor | 0.44 |
| Water** | | | 100 mL |

*Calculated at % w/w of total polymer.
**Not present in final formulation.

Example 5

A Fast Dissolving Film Which Provides a Sensory Impact

| Ingredient | % | Function | Amt/dose (mg) |
|---|---|---|---|
| Polyvinyl Alcohol-Polyethylene Glycol Graft Copolymer | 74.39 | Polymer | 59.31 |
| Nicotine Bitartrate | 7.5 | Active | 6.00 |
| Glycerin | 7.84 | Plasticizer | 6.27 |
| Sucralose | 0.78 | Sweetener | 0.63 |
| Peppermint (oil) | 5.49 | Flavor | 4.39 |
| Micron Intensates #030692** | 4.00 | Sensory Impact Flavor | 3.20 |
| Water*** | | | 100 mL |

The films of examples 4 and 5 are produced by the following means: The polymeric component is added to deionized water with continuous stirring until well mixed. Subsequently, the nicotine active and all optional components are added and stirring is continued until the components are completely dissolved in the deionized water-polymeric mixture. The resulting composition is cast onto any suitable surface, such as a plexiglass plate or extruded by any means known in the art and dried to remove the bulk of the water content from the final product.

What is claimed is:

1. An orally dissolving film composition formed by the combination of
    a polymer consisting of a pre-neutralized enteric polymer selected from the group consisting of cellulose acetate phthalate, hydroxypropyl methylcellulose phthalate, polyvinylacetate phthalate, poly(ethylacrylate -methacrylic acid) copolymer, shellac, hydroxypropyl methylcellulose acetate succinate, poly (methyl vinyl ether/maleic acid) monoethyl ester, and poly(methyl vinyl ether/maleic acid) n-butyl ester and mixtures thereof;
    at least one alkaline buffering agent; and
    nicotine oil;
        wherein the orally dissolving film is effective to reduce nicotine cravings within about 10 minutes through transbuccal absorption of nicotine.

2. The film composition of claim 1 wherein the pre-neutralized enteric polymer is poly(ethylacrylate-methacrylic acid) copolymer.

3. The film composition of claim 1 wherein said alkaline buffering agent is selected from the group consisting of sodium carbonate, sodium bicarbonate, potassium carbonate, potassium bicarbonate, sodium phosphate dibasic, sodium phosphate tribasic, potassium phosphate dibasic, potassium phosphate tribasic, calcium carbonate, magnesium carbonate, sodium hydroxide, magnesium hydroxide, potassium hydroxide, aluminium hydroxide, and mixtures thereof.

4. The film composition of claim 1 further comprising a plasticizer.

5. A method of reducing or eliminating tobacco consumption by an individual in need thereof by administering to the individual an orally dissolving film formed by the combination of polymer consisting of an enteric polymer selected from the group consisting of cellulose acetate phthalate, hydroxypropyl methylcellulose phthalate, polyvinylacetate phthalate, poly(ethylacrylate -methacrylic acid) copolymer, shellac, hydroxypropyl methylcellulose acetate succinate, poly (methyl vinyl ether/maleic acid) monoethyl ester, and poly(methyl vinyl ether/maleic acid) n-butyl ester and mixtures thereof, selected from the group consisting of cellulose acetate phthalate, hydroxypropyl methylcellulose phthalate, polyvinylacetate phthalate, poly(ethylacrylate -methacrylic acid) copolymer, shellac, hydroxypropyl methylcellulose acetate succinate, poly (methyl vinyl ether/maleic acid) monoethyl ester, and poly(methyl vinyl ether/maleic acid) n-butyl ester and mixtures thereof, nicotine oil and at least one alkaline buffering agent;
    wherein the orally dissolving film is effective to reduce nicotine cravings within about 10 minutes through transbuccal absorption of nicotine.

6. A method of providing rapid nicotine craving relief to an individual in need thereof by administering to the individual an orally dissolving film formed by the combination of a polymer consisting of an enteric polymer, nicotine oil and at least one alkaline buffering agent;
    wherein the orally dissolving film is effective to reduce nicotine cravings within about 10 minutes through transbuccal absorption of nicotine.

7. An orally dissolving film composition formed by the combination of
    a polymer consisting of an enteric polymer selected from the group consisting of cellulose acetate phthalate, hydroxypropyl methylcellulose phthalate, polyvinylacetate phthalate, poly(ethylacrylate -methacrylic acid) copolymer, shellac, hydroxypropyl methylcellulose acetate succinate, poly (methyl vinyl ether/maleic acid) monoethyl ester, and poly(methyl vinyl ether/maleic acid) n-butyl ester and mixtures thereof;
    at least one alkaline buffering agent; and
    nicotine oil;
        wherein the orally dissolving film is effective to reduce nicotine cravings within about 10 minutes through transbuccal absorption of nicotine.

8. A method of reducing or eliminating tobacco consumption by an individual in need thereof by administering to the individual an orally dissolving film formed by the combination of polymer consisting of a pre-neutralized enteric polymer selected from the group consisting of cellulose acetate phthalate, hydroxypropyl methylcellulose phthalate, polyvinylacetate phthalate, poly(ethylacrylate-methacrylic acid) copolymer, shellac, hydroxypropyl methylcellulose acetate succinate, poly (methyl vinyl ether/maleic acid) monoethyl ester, and poly(methyl vinyl ether/maleic acid) n-butyl ester and mixtures thereof, nicotine oil and at least one alkaline buffering agent;
    wherein the orally dissolving film is effective to reduce nicotine cravings within about 10 minutes through transbuccal absorption of nicotine.

9. A method of providing rapid nicotine craving relief to an individual in need thereof by administering to the individual an orally dissolving film formed by the combination of a polymer consisting of a pre-neutralized enteric polymer selected from the group consisting of cellulose acetate phthalate, hydroxypropyl methylcellulose phthalate, polyvinylacetate phthalate, poly(ethylacrylate -methacrylic acid) copolymer, shellac, hydroxypropyl methylcellulose acetate succinate, poly (methyl vinyl ether/maleic acid) monoethyl ester, and poly(methyl vinyl ether/maleic acid) n-butyl ester and mixtures thereof, nicotine oil and at least one alkaline buffering agent;
    wherein the orally dissolving film is effective to reduce nicotine cravings within about 10 minutes through transbuccal absorption of nicotine.

* * * * *